(12) United States Patent
Nieberding

(10) Patent No.: US 7,468,047 B2
(45) Date of Patent: Dec. 23, 2008

(54) ORTHOSIS AND METHOD FOR MANUFACTURE THEREOF

(75) Inventor: Reginald C. V. T. M. J. P. Nieberding, Kapellen (BE)

(73) Assignees: T Tape Company BV, Putte (NL); Ortopedijos Klinika UAB, Kaunas (LT)

( * ) Notice: Subject to any disclaimer, the term of this patent is extended or adjusted under 35 U.S.C. 154(b) by 0 days.

(21) Appl. No.: 11/814,033

(22) PCT Filed: Jan. 24, 2006

(86) PCT No.: PCT/EP2006/000597

§ 371 (c)(1),
(2), (4) Date: Jul. 16, 2007

(87) PCT Pub. No.: WO2006/077158

PCT Pub. Date: Jul. 27, 2006

(65) Prior Publication Data

US 2008/0103423 A1     May 1, 2008

(30) Foreign Application Priority Data

Jan. 24, 2005    (WO) ............... PCT/EP2005/000662

(51) Int. Cl.
*A61F 5/00*     (2006.01)
(52) U.S. Cl. .................... 602/7; 602/5; 602/17; 602/19

(58) Field of Classification Search ................. 602/6–8, 602/20, 23, 27
See application file for complete search history.

(56) References Cited

U.S. PATENT DOCUMENTS

| 3,253,600 | A | 5/1966 | Scholl |
| 4,676,801 | A | 6/1987 | Lundeen et al. |
| 4,888,225 | A | 12/1989 | Sandvig et al. |
| 6,595,938 | B1 | 7/2003 | Delmore et al. |

FOREIGN PATENT DOCUMENTS

| DE | 199 18 314 | 11/1999 |
| GB | 574 529 | 1/1946 |

OTHER PUBLICATIONS

International Search Report dated Mar. 17, 2006.

*Primary Examiner*—Kim M Lewis
(74) *Attorney, Agent, or Firm*—Knobbe, Martens, Olson & Bear, LLP

(57) ABSTRACT

A pre-fabricated orthosis suitable for embracing and supporting a body part of a human or animal is disclosed. The orthosis has an articulation and may be made from a pre-formed sheet of material containing cork and a thermoplastic binder. The orthosis may be uniformly perforated in its central part and may be composed of a mixture of cork and ethyl vinyl acetate (EVA). A method of manufacturing the orthosis is also disclosed.

27 Claims, 2 Drawing Sheets

ORTHOSIS AND METHOD FOR MANUFACTURE THEREOF

RELATED APPLICATIONS

This application is the U.S. National Phase under 35 U.S.C. §371 of International Application PCT/EP2006/000597, filed Jan. 24, 2006, which claims priority to PCT/EP2005/000662, filed Jan. 24, 2005.

FIELD OF THE INVENTION

The present invention relates to the medical field, and regards an orthosis (brace) for immobilizing, embracing and supporting a body part, preferably comprising an articulation. The invention also relates to a method for the manufacture of said orthosis.

BACKGROUND

Immobilization devices such as a cast, a splint, a brace (orthosis) and stiffening apparatuses are used to impart a desired position to a supported portion of the body or to immobilize the supported portion relative to other parts of the body. Traditionally, plaster casting materials have been used because they are very low cost. However, plaster casting materials are heavy and cannot be cleaned or easily removed. Recently, plaster casting materials have been replaced by synthetic casting materials which are lighter in weight and can be cleaned but have a rough exterior surface and are still relatively heavy and bulky.

This plaster material however shows some important disadvantages such as its weight, the development dust, the occurrence of sharp and hard edges, and the time required for its application. In addition, it is also often necessary that a cast or other immobilization device be removed for medical consultation or exercise by a therapist and then put back on the patient. The plaster material casts cannot be removed intact and put back on the patient.

Braces have been described which are made of a sheet material impregnated or coated with a curable resin. For instance, U.S. Pat. No. 6,595,938 discloses an orthopedic casting article. In one embodiment, the article comprises a flexible sheet material impregnated or coated with two different resins. The article may be in the form of an orthopedic casting tape or a protective pad comprising a fabric backing that is longitudinally impregnated or coated with two different curable resins, preferably water-curable resins. The orthopedic casts are made by providing a curable casting tape; initiating the cure of the casting tape, e.g., by exposing the casting tape to water; and allowing the casting tape to cure to form an orthopedic cast.

Also U.S. Pat. No. 6,100,206 discloses orthopedic casting article comprising a curable resin, e.g. a water curable resin, and a filler associated with the resin, e.g. fibrous materials.

Another example of an orthopedic cast is disclosed in U.S. Pat. No. 4,888,225, which is directed to a splint comprising a sheet formed of an open-celled foam sheet impregnated with a water curable resin. Upon activation of the resin impregnated foam sheet and molding the same around the body part, an orthopedic splint is formed.

However, a common drawback of the braces comprising a curable resin is that the curing process takes a considerably time, e.g. around 30 minutes or more, before an orthopedic cast, which functional enough to support the injury is obtained. Moreover, the curing process is irreversible and it is impossible to shape the cured cast or splint in another position. Therefore the cast or splint has to be changed, i.e. one need to apply again a new cast or splint, in different phases of the healing process of the injury. In addition, to supply the cast or splint a physician needs to wear gloves.

Another problem is that casting or splinting may be very difficult, especially when it is required to build casts having different angles, e.g. a 90° angle between the foot joint and low leg, since at the same time it is necessary to make sure that a good angle is obtained, that the lamination and pressure is optimal, that contours are followed, etc. Furthermore, a cast or splint like those present in the prior art, wherein the casting material consists of a water-curable resin, and/or currently used products such as synthetic casts and/or P.O.P. (Plaster of Paris), have a cure (setting) time that can take more than one hour. During all that time the chosen casting position needs to be maintained, otherwise the casting material can loose the wanted position and it might be required to start all over again. It is very difficult to keep a patient for 30 minutes or more to up to one hour or more to sit still when he/she is in pain, or when he/she is, like most children, scared.

Thermoplastic materials are now being used for forming casts and braces and other immobilization devices. These thermoplastic materials can be produced in extruded sheets which, when brought to a melt point (50° C. to 100° C.), can be molded and manipulated to conform to and shape around a body part, such as a limb, and then allowed to cool to hardness. These materials can also be reheated, brought back to their original shape and then remolded into a different shape. Compared to other casting materials, the thermoplastic materials provide many advantages including simplicity of use and ease of cleaning.

U.S. Pat. No. 6,093,161 describes a thermoplastic apparatus for immobilization or support of a body part of a human or animal. The apparatus is formed from a sheet of thermoplastic moldable material that is substantially rigid at ambient temperatures and pliable at higher temperatures. The apparatus consists of two elements, which are fastened to one another by means of a fastener for fastening. The fastener is directly attached to the thermoplastic material, so that the fastener allows the thermoplastic apparatus to be removed from and put back on the human or animal body part.

However, a problem associated with the above-mentioned braces made of thermoplastic material is that they lack flexibility, and do not allow the injured body part to undergo slight movements, e.g. swelling. In addition, differences in pressure in the brace (orthosis), e.g. due to movements of a patient carrying the brace or due to swelling of the body part, may induce deformations or distortions in the brace configuration and/or create pressure contacts on the body part. In addition, application of the above-mentioned type of braces on impaired limbs, arms or other body parts, involves the adjustment and fastening of the fasteners to a patient, which is a time-demanding process. Another problem associated with this type of braces is that they are relatively heavy.

It has been suggested to use cork-like material for manufacturing braces and the like. NL 1013907 for instance describes a splint made of a disposable material containing a cork-like material such as EVA (ethylene vinyl acetate). However, a problem associated with such material is that it is not breathable. This is an important disadvantage, since for improving wound heeling and for permitting better transpiration, it is highly recommended to use braces or the like which are capable of some oxygen/air diffusion. It has been shown in the art that braces that are not sufficiently breathable can cause skin irritation, skin maceration, or skin dryness.

Another problem with currently known braces made of softer materials, is that the braces may be or become too soft once applied on a body part, and lose sufficient hardness, such that such braces may easily bend or form folds or pressure contacts on the body part, which may cause injury or suboptimal recovery of the injured limb or joint.

The present invention seeks to remedy at least some of the aforementioned problems and drawbacks of the currently available immobilization devices, and offers other advantages over the prior art. In particular, it is an aim of the present invention to provide an orthosis showing improved flexibility but of a sufficient hardness. It is also an aim of the invention to provide an orthosis, which is breathable and comfortable. It is also an aim to provide an orthosis that allows facilitated and faster application on an injured body part.

SUMMARY

The present invention provides a pre-formed orthosis, which solves at least some of the above-mentioned problems.

The present invention provides in a first aspect an orthosis suitable for embracing and supporting a body part of a human or animal comprising an articulation which consists of a single sheet of natural material containing a binder, wherein said natural material is flexible and breathable. Another name for an orthosis is a brace. It is generally prescribed by a physician to provide correction, support, or protection to a part of the body. The present orthosis is light-weight, sanitary, and moisture-resistant. The orthosis is designed to maintain the body part in an optimal position for development and treatment.

The present orthosis is made of a flexible and breathable material. The term "flexible" as used herein, refers to a material which is able to adjust readily to different conditions and in particular refers to a material which is able to easily flex and/or bend without breaking.

As used herein the term "breathable" refers to a material, which allows air to pass to some degree. Such materials keep out water, but also release perspiration/transpiration vapor. This term may refer to materials that are naturally breathable, and for instance materials having a porous surface through which air can pass. This term may also refer to materials that have been made breathable by means of human mediation, for instance by means of perforation.

In a preferred embodiment, the invention is directed to a pre-fabricated orthosis suitable for embracing and supporting a body part of a human or animal comprising an articulation, said orthosis consisting of a pre-formed sheet of material comprising cork and a thermoplastic binder.

A particular characteristic of the present orthosis is that although the orthosis is flexible, it provides sufficient rigidity to the injured body part. More in particular, the present orthosis is made of a material comprising a combination of cork and a thermoplastic binder; such as preferably ethylene vinyl acetate (EVA). Cork is a moisture-adsorbent material, while the applied thermoplastic binder is a moisture repellent material. Surprisingly, it has been found by the applicant that by combining two materials having different and contradicting properties, an orthosis can be made which has optimal characteristics of hardness and flexibility. The present orthosis is due to its flexibility particularly suitable for allowing an injured body part to undergo slight movements, e.g. swelling. The orthosis is made of flexible material such that it is suitably deformable in order to conform to contours and the physical reactions of the treated body part (e.g. swelling/de-swelling). However, surprisingly this flexibility does not challenge the orthosis' rigidity and hardness.

In another preferred embodiment the orthosis is perforated. Preferably, the present orthosis has perforations in generally about 75% to 95% of its total surface area. In addition, because the material by which it is fabricated, and especially the cork, is breathable, the orthosis is comfortable to wear; it allows perspiration/transpiration and improves wound heeling. Problems of skin irritation or skin maceration can advantageously be diminished.

The present orthosis may be shaped in a configuration which is suitable for treating a human or animal body part preferably comprising an articulation such as elbow, ankle or wrist. In a preferred embodiment, the present orthosis is made of sheet of material, which is shaped into a configuration showing two elements which are fixed to each other under a fixed angle by means of an articulation. Thus, according to the present invention a pre-fabricated orthosis is provided, wherein the two elements of the orthosis are already fixed to each other under a fixed angle. An orthosis having a fixed angle between the different elements, in combination with its flexibility, has the major advantage that problems of obtaining a good angle are solved. Due to the braces' flexibility, a physician may easily fit the orthosis to the injured body parts and adjust the angle by gently allowing the flexible brace to adopt the contours of the injured body parts. In addition, if necessary, by temporarily and locally heating the material of the orthosis, a fixed angle may be easily bent if required to adopt another desired position. The present orthosis is thus easy to use, fast to use since it is pre-fabricated and there is no polymerization or setting time, and reliable to use, since the orthosis is always in a right position, with a high level of patient comfort.

Furthermore the orthosis is easy and quick to install. The orthosis offers the advantage of being able to be easily and rapidly removed and reapplied to a human or animal body part. It can thus be recycled during injury healing. Because the orthosis consists of a single sheet of material and not of two or more separate elements which need to be affixed to each other by one or more fastening means, a physiotherapist or physician may rapidly apply and remove the orthosis to/from the injured body part.

The orthosis according to the present invention is further soft in order to provide optimal wearing comfort to the patient. The present orthosis is in particular very light, and even three to four times lighter than conventional braces made of thermoplastic material. Furthermore the orthosis is clean and free of dust. Advantageously, the orthosis is translucent for X-rays. The present orthosis can be worn until complete recovery of the injured body part. The present orthosis also has good shape hardness and improved resistance to abrasion.

Other advantages of the present brace are that it does not adsorb water, and that it can be applied without using any means, such as warmth, steam, water, etc. . . . Moreover, the present orthosis is flexible and of sufficient hardness at the same time, two characteristics which are often difficult to combine.

Other benefits and advantages of the invention will become apparent upon reading and understanding the below given specification and accompanying drawings.

DETAILED DESCRIPTION OF THE FIGURES

DETAILED DESCRIPTION OF THE INVENTION

Figure 1:
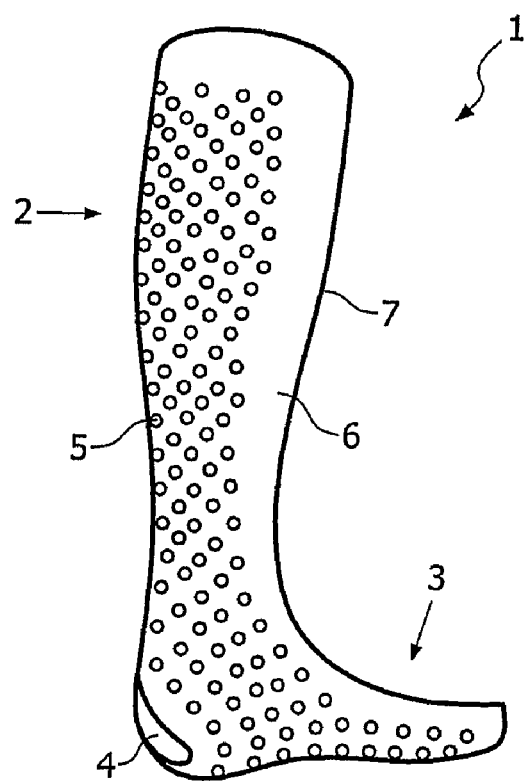
FIG. 1 illustrates an embodiment of an orthosis according to the present invention which is suitable for being applied in support of an ankle articulation.

The present invention relates to a pre-fabricated orthosis suitable for embracing and supporting a body part of a human or animal comprising an articulation. The orthosis consists of a pre-formed sheet of material comprising cork and a thermoplastic binder.

The terms "brace" and "orthosis" are used herein as synonyms.

The term "pre-fabricated" as used herein refers to an orthosis that has been made is a suitable configuration and that can be applied as such on a body part of a human or animal. A pre-fabricated orthosis, according to the present invention is thus ready to use, and does not need to be applied in the form of a curable casting tape or the like on a body part of a human or animal. The present orthosis does not have to be cured anymore and thus there is not setting time for applying the brace.

The term "pre-formed sheet" as used herein refers to a sheet that has been made of a material that can be used as such to fabricate the present orthosis.

In a preferred embodiment, said material has a Shore A which is comprised between 65 and 90, and more preferably comprised between 70 and 85, and for instance of 75. In another preferred embodiment, the present orthosis has a Shore A which is comprised between 65 and 90, and more preferably comprised between 70 and 85, and for instance of 75. Shore hardness is a measure of the resistance of material to indentation by an indenter. The "Shore A hardness" is the relative hardness of elastic materials such as rubber or soft plastics. A shore A measurement measures the resistance of the material toward indentation. The Shore A scale measures hardness of a material on a table from 0 to 100. The higher the measured value, the harder the material. If the indenter completely penetrates the sample, a reading of 0 is obtained, and if no penetration occurs, a reading of 100 results. The reading is dimensionless. The Shore hardness is measured with an apparatus well known as a Durometer and consequently is also known as 'Durometer hardness'. The hardness value is determined by the penetration of the Durometer indenter foot into the sample. Durometers for measuring a shore A scale are well known in the art and can be readily purchased and are therefore not described in detail herein. It shall be clear that the measurement of a Shore A value is a method well known to a skilled person in the art.

In yet another embodiment, the present orthosis has a shore A which is substantially similar over the complete surface of the orthosis. The present orthosis thus has a homogenous hardness.

In yet another embodiment, the shore A of the present orthosis remains constant and does not reduce in function of the time.

In yet another preferred embodiment, the material has a density comprised between 0.25 and 0.50 g/cm$^3$ and preferably comprised between 0.30 and 0.40 g/cm$^3$, and for instance of 0.35 g/cm$^3$. In a further embodiment, the present orthosis has a density comprised between 0.25 and 0.50 g/cm$^3$ and preferably comprised between 0.30 and 0.40 g/cm$^3$, and for instance of 0.35 g/cm$^3$.

The present invention relates to an orthosis suitable for embracing and supporting a body part of a human or animal. In general, the present orthosis may be used for support of arm joints, such as low arm, elbow, whole arm, hand, wrist, wrist with thumb, etc. . . . It may also be used for support of leg joints such as low leg, knee, hip, whole leg, feet, etc. . . . The present orthosis may also be used as corset for the complete back or parts thereof, for the neck, etc. . . . It may also advantageously be used as helmet for skull correction, e.g. for babies, or as 3D formed (pre-moulded) head support cushions, for use in nuclear medicine.

In a preferred embodiment, the present orthosis is particularly suitable for embracing and supporting a body part of a human or animal comprising an articulation. Examples of said body parts are limbs such as an arm, a leg, a foot, a hand, etc., the articulations of these limbs being an elbow, a knee, an ankle, a hip, a wrist, etc. Other possible body parts comprising an articulation may be neck, shoulder, back, collar, etc.

The orthosis consists of a single sheet of natural material containing a binder. The sheet of material may be shaped into a configuration showing one element. Such configuration may be very suited for being applied to e.g. a wrist, a wrist with thumb, hip, knee, shoulder, back, neck, collar (e.g. in the form of a corset), head (in the form of a helmet) etc. . . .

In another preferred embodiment, the sheet of material may be shaped into a configuration of a helmet and may be particularly suitable for being applied on the head, especially of kids.

Casting or splinting may be very difficult, especially when it is required to build in the different angles, e.g. a 90°, 100° or 110° angle between the foot joint and low leg, and at the same time it is necessary to make sure that the lamination and pressure is optimal, that contours are followed, etc. . . . Furthermore, a cast or splint like those present in the prior art, wherein the casting material consists of water-curable resins, and/or currently used products such as synthetic casts and/or P.O.P. (Plaster of Paris), have a cure (setting) time that can take more than one hour. During all that time the chosen casting position needs to be maintained, otherwise the casting material can loose the wanted position and it might be required to start all over again. It is very difficult to keep a patient for 30 minutes to up to one hour or more to sit still when he/she is in pain, or when he/she is, like most children, scared. The present orthosis does not have to be prepared in situ, but is a pre-fabricated orthosis, as indicated above. In addition, in yet another preferred embodiment, the sheet of material used to make the orthosis is shaped into a configuration showing two elements, which are fixed to each other under a fixed angle by means of an articulation. Such configuration may be very suited for being applied to e.g. an ankle or elbow. Suitable examples of fixed angles between said extending elements comprise angles having a value comprised between 80 and 120°, and comprise for instance 90°, 100° or 110°. According to the present invention a pre-fabricated orthosis is thus provided, wherein the two elements of the orthosis are already fixed to each other under a fixed angle. The present orthosis is thus provided, with a fixed angle between two elements thereof, such as for instance in an elbow-, low leg- or 110° orthosis according to the present invention. Furthermore, the present invention provides an orthosis wherein the fixed angle may be adapted; for instance with the aid of heat. By temporarily and locally heating the material, a fixed angle may be easily bent if required to another desired position. The present orthosis is easy to use, fast to use since it is pre-fabricated and there is no polymerization or setting time, and reliable to use, since the orthosis is always in a right position, with a high level of patient comfort.

A fixed angle between the brace parts is particularly advantageous in terms of easiness, rapidity and reliability, with a high level of patient comfort.

The orthosis according to the present invention can be used for tendon repairs and fractures and it can also be used for stabilization following sprains and strains, and in the presence of arthritis, tendonitis and cumulative trauma injuries. The orthosis can also be used for a wide variety of casts, splints and braces including wrist splints, cervical collars, lumbosacral immobilizers, upper and lower extremity supports, thoracic supports, knee immobilizers, and ankle orthosis and is therefore not intended to be limited by the following examples shown in FIGS. 1-4 of the drawings.

In a preferred embodiment the present orthosis is made of a flexible material comprising cellulose, preferably cork, and a binder, preferably a thermoplastic binder.

The use of cork in the present orthosis has the advantage that cork has initial strength. The cork thus contributes to the stability and strength of the present orthosis. Cork is a natural flexible and tough component which makes the material—in combination with a thermoplastic binder, such as e.g. EVA—very suitable for functional bracing or splinting. Furthermore, cork is a natural and environmental friendly component.

The binder is preferably a thermoplastic binder. Suitable thermoplastic polymers include polyurethanes (especially polyurethanes based on semi-crystalline polyester polyols), polyethylene, ethylene vinyl acetate (EVA), cis and trans polyisoprene, polyesters such as polycaprolactone and the like. The currently preferred binder for use in the present invention is preferably a rubber, such as a synthetic rubber, preferably an acetate polymer and most preferably EVA (ethyl vinyl acetate). EVA is durable plastic foam material made of ethylene vinyl acetate resin. EVA-containing material is sufficiently deformable, but still offers adequate rigidity for the application in an orthosis according to the present invention. In practice the orthosis containing EVA material will easily fit the contour of the body part to which is it fixed. EVA feels soft on the skin, does not induce allergic reactions on the skin and is X-ray translucent. The material can be advantageously made at low production costs and has a natural appearance.

In a particularly preferred embodiment, the present orthosis is made of a pre-formed sheet of material comprising cork and EVA. Preferably, the used material contains at least 20 weight % of cork, and at least 40 weight % of EVA. In an example the present material comprises 1 kg of cork for 4; 4.5; 5; 5.5; 6; 6.5; 7; 7.5; or 8 kg of EVA.

The combination of cork and EVA gives the material unique characteristics which cannot be gained with a combination with for instance of other material such as for instance cotton or cellulose with EVA. As mentioned above, although cork and EVA are two materials having different and contradicting properties, they can be advantageously combined to provide an orthosis of a surprisingly good flexibility and sufficient rigidity and hardness. An advantage of combining cork with EVA is the possibility to obtain an orthosis having an optimal strength, flexibility and toughness, which is needed for functional stabilization or immobilization of human and/or animal injuries. The combination of cork with EVA makes it possible to control both strength and flexibility. Furthermore the combination makes the brace water repellent which make the brace reusable by one patient.

In another preferred embodiment, the material may further contain additives and/or colorants. In a preferred embodiment of the present invention, these additives may comprise metal oxides. In an example, the present orthosis consists of cork material that has been pulverised and mixed with acetate polymers and ethyl vinyl in the presence of the metal oxide additives such as silicum oxide (preferably 15-20% w/v), aluminium oxide (preferably 5-10% w/v), zinc oxide (preferably 1-2% w/v), iron oxide (preferably 0.1-1% w/v), sodium, potassium and calcium oxide (preferably 0.1-0.5% w/v), and titan dioxide (preferably 0.01-1% w/v). The material may be provided as foamed and cross-linked microcellular solid with or without colorants. This material may be extruded and/or injected, e.g. in a pre-formed mold or the like.

In another preferred embodiment, the present invention provides an orthosis, wherein the material further comprises a hardening agent and/or a foaming agent. Preferably the material comprises at most 10 weight % of a hardening agent, and preferably between 2 and 8% by weight, and for instance 8%; 5%; 4%; 3% or 2% by weight. In another preferred embodiment, the material comprises at most 10 weight % of a foaming agent, and preferably between 2 and 8% by weight, and for instance 8%; 5%; 4%; 3% or 2% by weight.

Any appropriate hardening agent may be used in processes of the invention, including, for example but not limited to epoxy resins, sulphur sources, peroxides, metal oxides, amines and phenolic resins, etc.

Any appropriate foaming agent may be used in processes of the invention, including, for example but not limited to, water, low- boiling point hydrocarbons, hydrofluorocarbons or chlorofluorocarbons. Also gases or readily volatile inorganic or organic substances may be used as foaming agents. Examples of suitable organic foaming agents include acetone, ethyl acetate, halogen-substituted alkanes or perhalogenated alkanes, as well as butane, pentane, cyclopentane, hexane cyclohexane, heptane or diethyl ether. Examples of suitable inorganic foaming agents include air, $CO_2$ and $N_2O$. A foam formation effect may also be achieved by the addition of compounds which decompose at temperatures above room temperature with the evolution of gases, for example nitrogen and/or carbon dioxide, such as azo compounds, e.g. azodicarbonamide or azoisobutyronitrile, or salts such as ammonium bicarbonate, ammonium carbamate or ammonium salts of organic carboxylic acids, e.g. monoammonium salts of malonic acid, boric acid, formic acid or acetic acid.

A range of sizes of the orthosis can be produced, for example from extra small to extra large so as to enable the orthosis to be able to generally conform to and encircle a pre-selected human or animal body part. Another advantage is that because the present orthosis is made of a flexible material, it can easily be adjusted and cut with a scissor to the desired measurements. In a preferred embodiment, the surface of the orthosis according to the present invention is trimmed (polished). The present braces may be made for left or right body parts.

The configuration of the present orthosis is efficacious: after application of the orthosis preferably only in less than 5% of the cases the position of the orthosis on the injured body part had slightly changed however in acceptable proportions.

As mentioned above, the orthosis is made of breathable material. Such natural material may consist of a cell material, which is naturally breathable. The term "cell material" as used herein refers to material, which allows air to pass to some degree, for instance materials having a porous surface through which air can pass.

In another embodiment, the orthosis according to the present invention is perforated. In a preferred embodiment the sheets of flexible material are perforated prior to cutting the sheets into the desired shape. Perforations permit ventilation of the skin when the orthosis is placed upon a body part of a human patient. Preferably, between about 75-95% of the total surface area of the orthosis is perforated, and for instance 75; 80; 85; 90 or 95% of the total surface area of the orthosis is perforated. This amount of perforation will provide adequate strength to the orthosis while allowing for good air circulation, which will improve skin ventilation and wound heeling as compared to non-perforated and/or non-breathable braces. In a preferred embodiment, the orthosis has a number of perforations comprised between 60 and 125 per 1 $dm^2$, and preferably comprised between 75 and 115 per $dm^2$, and for instance of 100 per $dm^3$. The perforations are generally uniform and the diameter of the perforations is generally in the range of about 3.5 mm to 8.0 mm, with preferred diameter to be generally about 6.5 mm. Alternatively, perforations over a smaller percentage of surface area will provide only slight ventilation. In a particularly preferred embodiment, only the central portion of the orthosis is provided with perforations, and the orthosis is free of perforations in a zone of about 10 to 60 mm and typically about 30 mm from the edges of the orthosis. Absence of perforations in this zone permits to avoid that perforations would tend to be torn or worn out under influence of forces applied on the orthosis when worn by a patient.

In another preferred embodiment, the orthosis provided with blunt or "rounded" edge. The orthosis does not show sharp edges of portions which could harm and/or wound the injured body part to which the orthosis is applied.

The thickness of the orthosis is preferably at least 2 mm and will preferably b less than about 30 mm. In a preferred embodiment, the thickness of the orthosis may range from about 3 mm to 8 mm, with a preferred thickness of for instance 4, 5, 6 or 8 mm. When the orthosis is used for support of the hand, a thinner orthosis is preferable and when the orthosis is used as an immobilization orthosis for the lower extremities, a thicker orthosis is preferred. A variety of thicknesses of the orthosis can be formed into sheets in which the appropriate thickness is chosen for the desired support of the pre-selected body part. Selecting a sheet of the appropriate thickness will eliminate excess bulk in the weight of the orthosis.

Advantageously, the present orthosis is considerably lighter that prior art splints or braces. An orthosis according to the present invention preferably has a weight higher then 50 gram but preferably less than 400 gram.

In another preferred embodiment, the orthosis according to the present invention has the following characteristics as represented in table 1.

TABLE 1

Technical parameters of a preferred embodiment of an orthosis according to the invention

| Parameter | Standard | unit | Value |
|---|---|---|---|
| Hardness | ASTM D-2240 | Shore A | 69-90 |
| Density | — | $G/cm^3$ | 0.25-0.35 |
| Tensile strength | NF T 46-002 | $DaN \cdot cm^2$ | 16-27 |
| Elongation | NF T 46-002 | % | 50-100 |
| Abrasion | NF G 62-001 5N | $mm^3$ | 300-350 |

Figure 2:
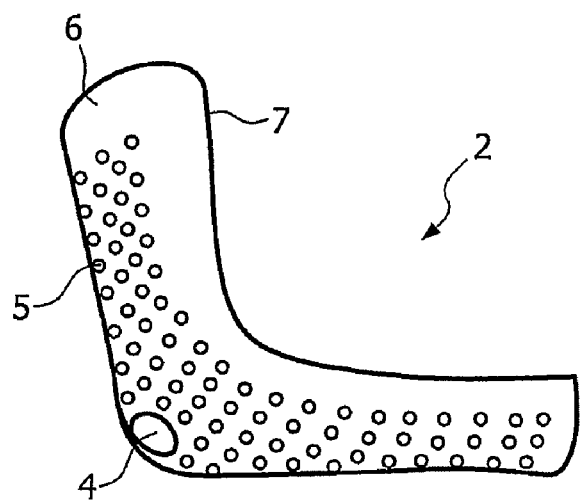
FIG. 2 illustrates an embodiment of an orthosis according to the present invention which is suitable for being applied in support of an elbow articulation.
Figure 3:
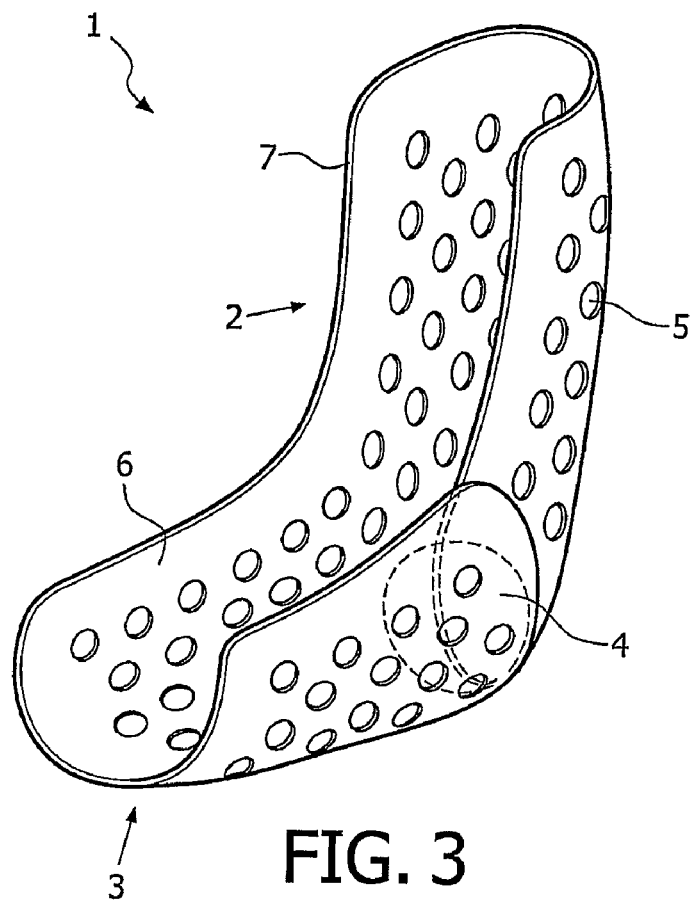
FIG. 3 is a perspective view of an embodiment of an orthosis according to the present invention which is suitable for being applied in support of an elbow articulation.
Figure 4:
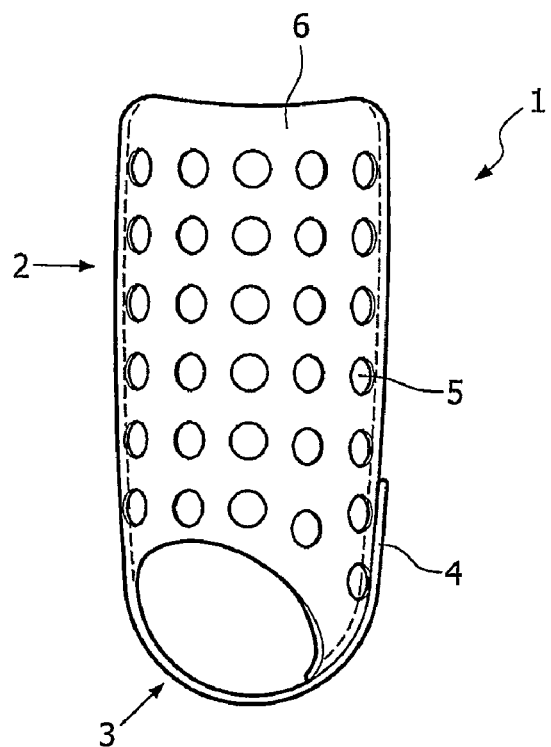
FIG. 4 is a frontal view of an embodiment of an orthosis according to the present invention, which is suitable for being applied in support of an elbow articulation.

Preferred examples of an orthosis 1 according to the present invention involve a low leg orthosis (FIG. 1) and an elbow orthosis (FIG. 2-4). Referring to the figures, the represented orthosis shows two elements 2, 3, which are fixed to each other under a fixed angle by means of an articulation 4. The orthosis has perforations 5 which are uniformly distributed on its total surface area, except for a small area 6 departing from the edges 7 of the orthosis. The fixed angle between said extending elements 2, 3 is about 90°.

In table 2, a number of different embodiments of braces according to the present invention are represented, indicating preferred thicknesses of the braces. However, it will be clear that other braces having other thicknesses may be provided as well according to the present invention.

TABLE 2

| Description | thickness of the material |
|---|---|
| Low arm splint, Small/medium size, Left or Right, trimmed, perforated | 4 mm or 5 mm |
| Low arm splint, Medium/Large size, Left or Right, trimmed, perforated | |
| Knee Brace, Small/Medium size, Left or Right, trimmed, perforated | 8 mm |
| Knee Brace, Medium/Large size, Left or Right, trimmed, perforated | |
| Low leg Brace, Small size, Universal, trimmed, perforated | 5 mm or 6 mm |
| Low leg Brace, Medium size, Universal, trimmed, perforated | |
| Low leg Brace, Large size, Universal, trimmed, perforated | |
| Elbow brace, Small/Medium, Universal, trimmed, perforated | 5 mm |
| Elbow Brace, Medium/Large, Universal, trimmed, perforated | |
| Low leg Brace 110°, Small/Medium size, Universal, trimmed, perforated | 5 mm or 6 mm |
| Low leg Brace 110°, Medium/Large size, Universal, trimmed, perforated | |
| Humerus Brace, Small/Medium size, Universal, trimmed, perforated | 5 mm |
| Humerus Brace, Medium/Large size, Left or Right, trimmed, perforated | |
| Intrinsic plus Position Splint, Small/Medium size, left or right, trimmed, perforated | 6 mm |
| Intrinsic plus Position Splint, Medium/Large size, left or right, trimmed, perforated | |
| Low arm splint, Paediatric-Small, Paediatric-Medium, or Paediatric-Large, Left or Right, trimmed, perforated | 4 mm |
| Low leg Brace, Paediatric-Small, Paediatric-Medium, or Paediatric-Large, Universal, trimmed, perforated | 5 mm |
| Elbow brace, Paediatric-Small, Paediatric-Medium, or Paediatric-Large Universal, trimmed, perforated | 5 mm |

In another aspect, the present invention relates to a sheet of material, preferably in the configuration of a roll or a plate, for manufacturing an orthosis according to the present invention, comprising cork and a thermoplastic binder, as defined herein. Preferably said sheet of material further comprises additives and/or colorants selected from the group comprising metal oxides as those defined herein. In another preferred embodiment, said sheet of material further comprises a hardening agent and/or a foaming agent, as defined herein. Preferably said sheet of material has a shore A comprised between 65 and 90, and preferably between 70 and 85, and for instance of 75. Also, it is preferred that said material has a density comprised between 0.25 and 0.50 $g/cm^3$, and preferably comprised between 0.30 and 0.40 $g/cm^3$, and for instance of 0.35 $g/cm^3$. The amounts of components in the present sheet of material are as defined herein.

In another aspect, the invention relates to a method for manufacturing an orthosis for embracing and supporting a body part of a human or animal. The method comprises the steps of:

a) selecting a sheet of a material comprising cork and a thermoplastic binder, b) cutting said sheet of material, in order to obtain a pre-cut sheet, c) molding and shaping of the pre-cut sheet of step c) into a configuration suitable for embracing and supporting a body part, d) allowing the molded and shaped sheet of step c) to cool and harden.

Preferably the sheet selected in step a) a pre-formed sheet of a material as defined herein.

Usually, the orthosis can be made by preliminary cutting out parts of the splint of patterns especially designed to be patient friendly. Semi-finished products are then heated on a heating plate at temperatures as indicated below. The semi-finished products are heated until the material becomes somewhat plastic. Depending on the thickness of the material this heating may take 1 to 2 minutes. After heating the material is lifted out, placed in a plaster model, corresponding to an arm joint, leg joint, neck, wrist, etc. . . . and then formed. Finishing may be obtained by means of polishing and if necessary by gluing.

More in particular, the orthosis according to the present invention is manufactured by taking a sheet of natural material containing a rubber, preferably a material containing cork and a rubber, such as EVA and cut in a selected shape (two dimensional plane). The pre-cut sheet is then softened in a heat transfer area, having a temperature of preferably between 75 to 130° C., and more preferably about 80 to 110° C., for at least 2 minutes. Depending upon the thickness of the flexible material used, the time the pre-cut sheet remains in the heat transfer area can range from about 1 to 5 minutes. The pre-cut sheet is then first partially molded and shaped to form a configuration which suitable for embracing and supporting a certain body part. Such configurations may involve two elements which are able to be fixed to each other under a fixed angle by means of an articulation. Then the molded and shaped sheet is allowed to cool and harden In the final shape. The orthosis hardens in place and cools after preferably about 5 to 10 minutes of molding time by a technician.

In another embodiment, the material containing a binder as defined herein is extruded in the form of a plate and subsequently reworked in the form of a splint or prosthesis. Such embodiment permits to obtain an orthosis which is of uniform smoothness and thickness.

In yet another embodiment, the material containing a binder as defined herein can be vulcanised in the form of a block and subsequently cut to a certain thickness.

If perforations are desired in the orthosis, the perforations are formed by punching out holes in the pre-cut sheet preferably before the sheet is softened. In a preferred embodiment, generally about 75-95% of the total surface area of the apparatus is perforated in order to provide ventilation. In another preferred embodiment, a zone of 10 to 60 mm departing from the edges of the orthosis remains free of perforations.

Optionally, the formed extending elements in the orthosis are affixed to each other under a certain fixed angle, preferably comprised between 80° and 120°, e.g. by gluing one extending element to another element under affixed angle. Any type of glue can be used for this purpose, and for instance wood glue.

In another preferred embodiment, the present selected sheet of material is obtained by mixing suitable amounts of cork and a thermoplastic binder, preferably EVA, which is of a suitable and sufficient liquid consistency, and optionally in the presence of suitable hardening and/or foaming agents. Preferably the mixing step of the components is performed at a temperature of between 75 to 130° C., and more preferably about 80 to 110° C.

The orthosis and method according to the invention are particularly suitable in the field of paramedical and orthotic applications. In particular the invention can be used for the treatment of all kind of injuries, especially of arm, elbow or knee and of hand or foot leg injuries. The present orthosis is also very suitable for the treatment of closed, non-complicated and stabile fractures, especially of children, as well as for treating severe distortions, complete or incomplete fractures or for post-operative immobilization. The present orthosis is further particularly suitable as a kind of first aid splint. The orthosis according to the present invention can be fixed to a body part by means of a stockinet, leather, sticky tape, elastic material, etc. . . .

The present orthosis is thus particularly advantageous because it doesn't need the aid of water (polymerization/curing) or other sources (like steam, heat, and others) to be cured. It is a ready to use product that can be applied on a patient without gloves and which is immediately functional A nurse or physician needs only about 1 to 2 minutes to put the orthosis in a right position, which is important in first aid centers and emergency rooms. Generally, also about 30 to 40 minutes are saved, because known synthetic braces are not suitable for being used post surgery, or are difficult to apply, or have major disadvantages, such as for instance releasing a lot of dust in the case of P.O.P. braces, such that intensive cleaning after each surgical or other medical intervention is required. The present orthosis does not release any dust.

Due to its unique characteristics the material will follow the contour of the body, and be easily applicable with the aid of a simple elastic bandage. Furthermore the present orthosis can be (re)used more often on the same patient, which is cost saving.

In addition, during each use the orthosis will adjust to the current shape of the injury area. The present orthosis can be applied, for instance, In case of fractures for:
    treatment/usage on first aid department, followed by,
    transport to X-ray department (material is completely X-ray translucent), followed by,
    post-operative treatment (after surgery), followed by,
    wound or other control of injury, all with one orthosis.

In the case of wounds for:
    treatment/usage on first aid department, followed by,
    wound or other control of injury, all with one orthosis.

It can also be applied in the case of transport from the place of an accident to the hospital.

During the healing process the fracture area will change from shape, like reducing of extending of the swelling before and after operation, etc. . . . The present orthosis will always follow the contours of the body, due to the fact that the present orthosis is flexible but stable and hard enough. However, the present orthosis can not be bent or folded.

With the aid of a scissor the present orthosis can be cut to a nearly custom made brace.

Furthermore the present orthosis can be easily cleaned with the help water or alcohol due to the fact that the present orthosis is water-repellent. Moreover, it also does not adsorb blood. The present orthosis needs not to be packed in an impermeable or airtight packing, since it will generally not absorb moisture from air.

The present orthosis is very light and therefore more pleasant to wear than conventional braces.

Although the present invention has been described with reference to its preferred embodiments, those skilled in the art will recognize changes which may be made in form or structure which do not depart from the spirit of the invention already described in the specification and embodied in the claims which follow.

What is claimed is:

1. A pre-fabricated orthosis suitable for embracing and supporting a body part of a human or animal comprising an articulation, said orthosis consisting of a pre-formed sheet of material comprising cork and a thermoplastic binder, and wherein said orthosis comprises a shore A between 65 and 90.

2. The orthosis according to claim 1, wherein said orthosis has a density between 0.25 and 0.50 g/cm$^3$.

3. The orthosis according to claim 1, wherein said pre-formed sheet of material is shaped into a configuration showing two extending elements which are fixed to each other under a fixed angle by means of an articulation.

4. The orthosis according to claim 3, wherein the fixed angle between said extending elements is between 80 and 120°.

5. The orthosis according to claim 1, wherein the orthosis has perforations in generally about 75% to 95% of its total surface area.

6. The orthosis according to claim 1, wherein the orthosis comprises a number of perforations between 60 and 125 per 1 dm$^2$.

7. The orthosis according to claim 6, wherein the orthosis comprises a number of perforations between 75 and 115 per dm$^2$.

8. The orthosis according to claim 1, wherein the orthosis is free of perforations in a zone of 10 to 60 mm from the edges of the orthosis.

9. The orthosis according to claim 1, wherein the orthosis comprises perforations showing a diameter between 3.5 and 8.0 mm.

10. The orthosis according to claim 1, wherein the pre-formed sheet of material comprises at least 20 weight % of cork.

11. The orthosis according to claim 1, wherein said thermoplastic binder is a synthetic rubber.

12. The orthosis according to claim 11, wherein said synthetic rubber is an acetate polymer.

13. The orthosis according to claim 1, wherein said thermoplastic binder is EVA (ethyl vinyl acetate).

14. The orthosis according to claim 1, wherein the pre-formed sheet of material comprises at least 40 weight % of EVA.

15. The orthosis according to claim 1, wherein said material further comprises additives and/or colorants selected from the group consisting of metal oxides.

16. The orthosis according to claim 1, wherein said pre-formed sheet of material further comprises a hardening agent and/or a foaming agent.

17. The orthosis according to claim 1, wherein the orthosis is between 2 and 30 mm thick.

18. The orthosis according to claim 1, wherein said orthosis comprises blunt edges.

19. The orthosis according to claim 1, wherein the orthosis has a weight between 50 and 400 gram.

20. A method for embracing and supporting a body part of a human or animal comprising an articulation comprising the step of fixing the orthosis according to claim 1 onto a body part of a human or animal.

21. A method for embracing and supporting a body part of a human or animal comprising applying the orthosis according to claim 1 to a body part of a human or animal as a corset or helmet.

22. A method for manufacturing an orthosis according to claim 1 for embracing and supporting a body part of a human or animal comprising the steps of:
   a) selecting a sheet of a material comprising cork and a thermoplastic binder,
   b) cutting said sheet of material, in order to obtain a pre-cut sheet,
   c) molding and shaping of the pre-cut sheet of step b) into a configuration suitable for embracing and supporting a body part,
   d) allowing the molded and shaped sheet of step c) to cool and harden.

23. The method according to claim 22, comprising perforating the pre-cut sheet prior to shaping and molding thereof.

24. The method according to claim 22, comprising molding and shaping of the pre-cut sheet of step b) into a configuration showing two elements which are able to be fixed to each other under a fixed angle by means of an articulation.

25. The method according to claim 24, further comprising the step of fixing one element to another element under a fixed angle.

26. The method according to claim 22, wherein said molding is performed at a temperature between 75° C. and 130° C.

27. The pre-fabricated orthosis according to claim 1, wherein said orthosis comprises a shore A between 70 and 85.

* * * * *

UNITED STATES PATENT AND TRADEMARK OFFICE
CERTIFICATE OF CORRECTION

| | | |
|---|---|---|
| PATENT NO. | : 7,468,047 B2 | Page 1 of 1 |
| APPLICATION NO. | : 11/814033 | |
| DATED | : December 23, 2008 | |
| INVENTOR(S) | : Reginald C. V. T. M. J. P. Nieberding | |

It is certified that error appears in the above-identified patent and that said Letters Patent is hereby corrected as shown below:

Column 8, Line 32, "CO2 and N2O." should be changed to --$CO_2$ and $N_2O$.--

Column 11, Line 34, "and harden In the" should be changed to --and harden in the--

Column 11, Line 55, "under affixed angle." should be changed to --under a fixed angle.--

Signed and Sealed this

Twenty-first Day of April, 2009

JOHN DOLL
*Acting Director of the United States Patent and Trademark Office*